(12) United States Patent
Smith

(10) Patent No.: US 6,292,102 B1
(45) Date of Patent: Sep. 18, 2001

(54) APPARATUS FOR DETECTING ENURESIS IN A PATIENT

(75) Inventor: Toby E. Smith, Broken Arrow, OK (US)

(73) Assignee: Bed-Check Corporation, Tulsa, OK (US)

(*) Notice: Subject to any disclaimer, the term of this patent is extended or adjusted under 35 U.S.C. 154(b) by 0 days.

(21) Appl. No.: 09/596,268

(22) Filed: Jun. 16, 2000

Related U.S. Application Data

(60) Provisional application No. 60/144,978, filed on Jul. 22, 1999.

(51) Int. Cl.⁷ ................................................ G08B 21/00
(52) U.S. Cl. ............................................ 340/604; 340/605
(58) Field of Search ............................. 340/573.1, 573.5, 340/604, 605; 128/885, 886, 897

(56) References Cited

U.S. PATENT DOCUMENTS

| | | | |
|---|---|---|---|
| 1,772,232 | 8/1930 | Van Guilder | 200/61.05 |
| 2,726,294 | 12/1955 | Kroening et al. | 200/61.05 |
| 3,778,570 | 12/1973 | Shuman . | |
| 3,864,676 | 2/1975 | Macias et al. . | |
| 3,971,371 | 7/1976 | Bloom . | |
| 4,069,817 | 1/1978 | Fenole et al. . | |
| 4,106,001 | 8/1978 | Mahoney . | |
| 4,191,950 | 3/1980 | Levin et al. . | |
| 4,212,295 | 7/1980 | Snyder . | |
| 4,347,503 | 8/1982 | Uyehara . | |
| 4,356,818 * | 11/1982 | Macias et al. | 128/886 |
| 4,484,573 | 11/1984 | Yoo . | |
| 4,502,044 | 2/1985 | Farris et al. . | |
| 4,539,559 | 9/1985 | Kelly et al. . | |
| 4,640,276 | 2/1987 | Jing-Sheng . | |
| 4,704,108 | 11/1987 | Okada et al. . | |
| 4,760,383 | 7/1988 | DiLorenzo . | |
| 4,843,305 * | 6/1989 | Akiba | 340/605 |
| 5,036,859 | 8/1991 | Brown . | |
| 5,043,704 | 8/1991 | Blakeney . | |
| 5,137,033 * | 8/1992 | Norton | 340/573.1 |
| 5,192,932 | 3/1993 | Schwab, Jr. . | |
| 5,315,291 * | 5/1994 | Furr | 340/605 |
| 5,760,694 * | 6/1998 | Nissim et al. | 340/604 |
| 5,790,036 | 8/1998 | Fisher et al. . | |
| 5,908,411 | 6/1999 | Matsunari . | |
| 6,147,613 * | 11/2000 | Doumit | 340/605 |

FOREIGN PATENT DOCUMENTS

| | | | |
|---|---|---|---|
| 1 200 974 | 8/1970 | (GB) | G01N/27/12 |
| 2 182 181 A | 5/1987 | (GB) | G08B/21/00 |
| WO 84/01626 | 4/1984 | (WO) | G01N/27/12 |

OTHER PUBLICATIONS

Search Results for "Enuresis" from the U.S. Patent & Trademark Office database, Jul. 13, 1999, list of 128 patents.
Search Results for "ABST/bed and ABST/wetting" from the U.S. Patent & Trademark Office database, Jul. 13, 1999, list of 25 patents.

\* cited by examiner

*Primary Examiner*—Van T. Trieu
(74) *Attorney, Agent, or Firm*—Fellers, Snider, Blankenship, Bailey & Tippens, P.C.

(57) ABSTRACT

This invention relates generally to patient monitoring systems and more particularly concerns devices and systems used to monitor bed patients in hospital or other care-giving environments. In accordance with a first aspect of the instant invention, there is provided a wetness detector for use in patient monitoring situations and which is adjustable in its degree of sensitivity to wetness. It contains at least two conductive regions placed on a non-conductive base and which are preferably separated laterally by some distance. Isolated electrical leads are attached to each conductive region. Electrical current passes much more readily between the two conductive regions when an electrolytic solution such as urine is present within the switch, thereby making it possible for a separate electronic monitor to determine when wetness is detected.

16 Claims, 4 Drawing Sheets

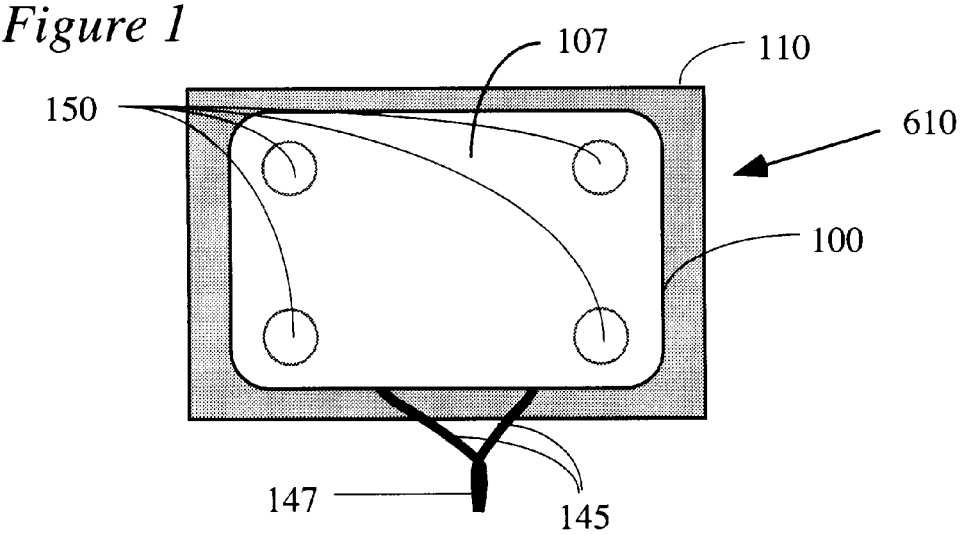
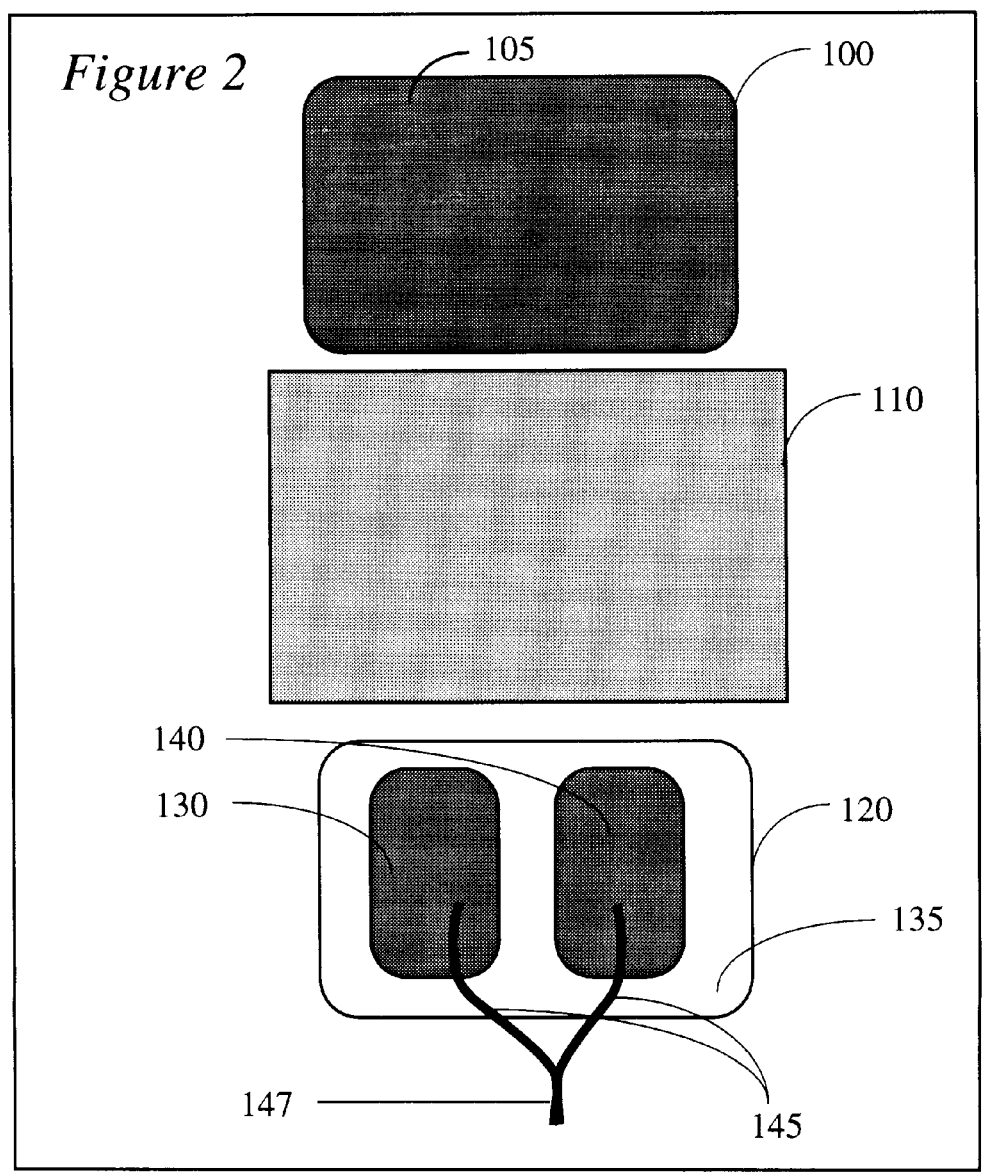

APPARATUS FOR DETECTING ENURESIS IN A PATIENT

RELATED APPLICATIONS

This application claims priority from provisional U.S. patent application Ser. No. 60/144,978 filed on Jul. 22, 1999, the disclosure of which is incorporated herein by reference.

FIELD OF THE INVENTION

This invention relates generally to the detection of electrically conductive solutions and, more particularly, concerns devices and systems used to monitor individuals for the discharge of urine, especially in a hospital or other health care setting.

BACKGROUND OF THE INVENTION

Incontinence is a familiar and predictable circumstance in the very young. However, the same problem can affect the elderly and/or the infirm of any age, who might have this problem because of some physiological, neurological, or psychological cause. Devices for detecting body fluids such as urine are particularly useful in institutional health care situations, where they are used to monitor and record urinary incontinence in bedfast patients.

As is well known to those of ordinary skill in the art, the trend nation-wide in patient monitoring has been toward the use of electrical devices to signal changes in a patient's circumstance to a care-giver who might be located either nearby or remotely at a central monitoring facility, such as a nurse's station. The obvious advantage of an electronic monitoring arrangement is that it frees the care-giver to pursue other tasks away from the patient. Additionally, when the monitoring is done at a central facility a single nurse can monitor multiple patients which can result in decreased staffing requirements. General information relating to mats for use in patient monitoring may be found in U.S. patent application Ser. No. 09/285,956 filed Apr. 2, 1999 the disclosure of which is specifically incorporated herein by reference. Additionally, U.S. Letters Patent Nos. 4,179,692, 4,295,133, 4,700,180, 5,633,627, and 5,640,145, the disclosures of which are incorporated herein by reference, contain further information generally pertinent to this same subject matter.

Among the advantages of electronic monitoring that are specifically applicable to the invention of the instant disclosure, it is well known that a signalling device can, in some circumstances, serve to condition the wearer to have improved bladder control, which can result in improved attitudes and state of psychological well being. Obviously, timely recognition of a problem has other advantages, including sanitary and aesthetic considerations.

Generally speaking, electronic patient monitors of the sort taught herein work by first sensing an initial status of a patient, and then generating a signal when that status changes, e.g., when the patient's bedclothes—which were formerly dry—become wet due to emission of urine. Electronic enuresis monitors typically exploit the fact that urine is a solution of, among other things, electrolytes, and will conduct a current of electricity. Detecting such fluids often has often involved using a pair of electrodes connected to a voltage source, and a detector circuit that activates an alarm when a gap between the electrodes is bridged by an electrically conductive fluid. Thus, presence of urine completes an otherwise "open" electrical circuit, which fact can be sensed by an attached electronic monitor. Those skilled in the art will recognize that the alarm might be local and/or remote (e.g., the monitor might signal the nurses station that a wetness has been detected).

However, there are serious risks associated with the use of electrical devices to detect fluid emissions, among which is the danger of galvanic burn to the monitored patient. In a typical arrangement, a constant load is applied to two electrical leads that are designed to be electrically isolated until such time as urine is present to bridge the connection. However, since electrical current is undiscriminating in the path that it takes—seeking, as it does, only the most direct way to complete the circuit—it is possible for the electrical current to pass through the patient's body (e.g., along the surface of the skin) when the circuit is completed. Alternatively, and much more dangerously, if the wet patient is grounded a serious electrical shock may be experienced. In spite of this fact, many monitoring pads sold today contain electrically conductive elements that come into near direct physical contact with the monitored individual during the time when those elements carry an electrical charge, thereby creating a risk of a galvanic burn of the patient's skin. Many more pads allow the patient's skin to come into electrical contact with the current used to monitor the device.

Further, many modem electronic monitors are susceptible to false alarms, a false alarm often being generated when the monitor becomes damp, rather than completely wet. Damp conditions might originate from, for example, perspiration. While excessive sweat is certainly a medical condition that could merit triggering an alarm in some instances, it should be under the control of the care giver as to whether or not this condition is signaled. Most electronic monitors are not designed with a minimum triggering wetness threshold level in mind and, thus, are subject to false alarms when they become damp.

Heretofore, as is well known in the patient monitor arts, there has been a need for an invention to address and solve the above-described problems. Accordingly, it should now be recognized, as was recognized by the present inventors, that there exists, and has existed for some time, a very real need for a enuresis mat and monitoring system that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided a binary switch-type device (e.g., a "mat") for use in patient monitoring situations where release of bodily fluids such as urine is a concern. The preferred switch is, broadly speaking, a "sandwich" construction that consists of two outer layers that are separated by a porus, non-conductive insulating layer. Each outer layer member is constructed of a material that is non-conductive to electrical current and impervious to fluids. In the preferred embodiment, the base material will be polyester or plastic. On the inner face of at least one outer layer—which inner faces are oriented so as to face each other across the insulating layer—is placed some sort of electrically conductive material, the preferred arrangement being that the electrically conductive material is aluminum and is placed on the inner face by vacuum deposition: i.e., aluminized polyester as it is sometimes referred to by those skilled in the art. Additionally, the conductive material preferably does not cover the entire surface of both faces, but portions of those faces have been left uncovered (either at the time of aluminum deposition or subsequently by a stripping action). It is critical for purposes of the instant invention that there be at discontinuous regions of conductive material on at least one face. The separation between the conductive regions is a parameter that can be used to help control the triggering level (e.g., how damp the switch must be before the sensing circuit is closed).

In the preferred embodiment, the central insulating layer will be sized so as to extend beyond the edges of the outer layer members—although that is not strictly necessary—thereby allowing it to contact (sense wetness in) a larger area than it would otherwise. It is essential, though, that the interior of the switch "sandwich" be in fluid communication with the exterior of the device because, if it were completely sealed from fluid contact with the exterior, this would thwart its principal purpose. On the other hand, some means must be used to fasten together the various layers in the sandwich: for example, either adhesive or heat-related means would be suitable. However, the process of fastening together the layers can create impermeable regions within the switch, which must not be too extensive. Thus, in the preferred embodiment the switch will not be completely sealed at its outer edges, but will be constructed in such a way as to allow fluid to migrate into interior.

The discrete conductive regions of the inner faces of the non-conductive members are placed in electrical contact with two electrically isolated leads. The precise position of the leads on the inner face(s) of the non-conductive layers will depend on the geometry of the conductive regions and the wetness event that it is desired to sense. It is critical, however, that if the switch is dry little or no current can be sensed across the electrical leads. On the other hand, when the switch is exposed to an electrolytic solution, that solution provides a pathway for electricity to move more freely from one lead to the other and thereby closes a circuit formed by the electrical leads and the various conductive regions within the switch. In that case, a monitor designed to follow the state of this circuit will be able to sense that moisture has been encountered and thereafter respond accordingly.

In operation, when the central insulating layer comes into contact with an electrolytic solution such as urine at its periphery, it will draw that liquid toward its center through capillary action. As the fluid penetrates into the center of the switch, it will complete/close electrical contacts, the precise nature of which will depend on the geometry of the conducting/nonconductive regions that have been placed on the two inward-facing faces. In the preferred embodiment, the geometry will be such that insulating layer must contain fluid in at least two different regions of the switch in order to close the monitoring circuit.

Note that in this preferred configuration, the patient is shielded from contact with the electrical leads by the non-conducting outer surfaces of the outer layers. This will have the effect of reducing or eliminating the likelihood of a patient experiencing galvanic burns after the monitor electrical elements become saturated.

According to another aspect of the instant invention, there is provided a monitor for use in conjunction with the previous switch which is designed to further protect the patient from galvanic burns. In more particular, rather than applying a constant load across the two isolated electrical leads, a pulsed voltage is applied to the leads, where pulsed is used in the broadest sense to include any cyclical electronic signal. In the preferred embodiment, the response to that voltage—a Faradic pulse—is monitored for evidence of completion of the switch circuit.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to cover all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which:

FIG. 1 illustrates a plan view of the switch portion of the instant wetness monitor.

FIG. 2 contains a schematic diagram that illustrates the various components of the preferred wetness monitor.

DETAILED DESCRIPTION OF THE INVENTION

General Background

According to a preferred aspect of the instant invention, there is provided a wetness sensor for use with an electronic patient monitor, wherein the sensor is configurable to require a predetermined degree of wetness before being fully responsive thereto.

Figure 6:
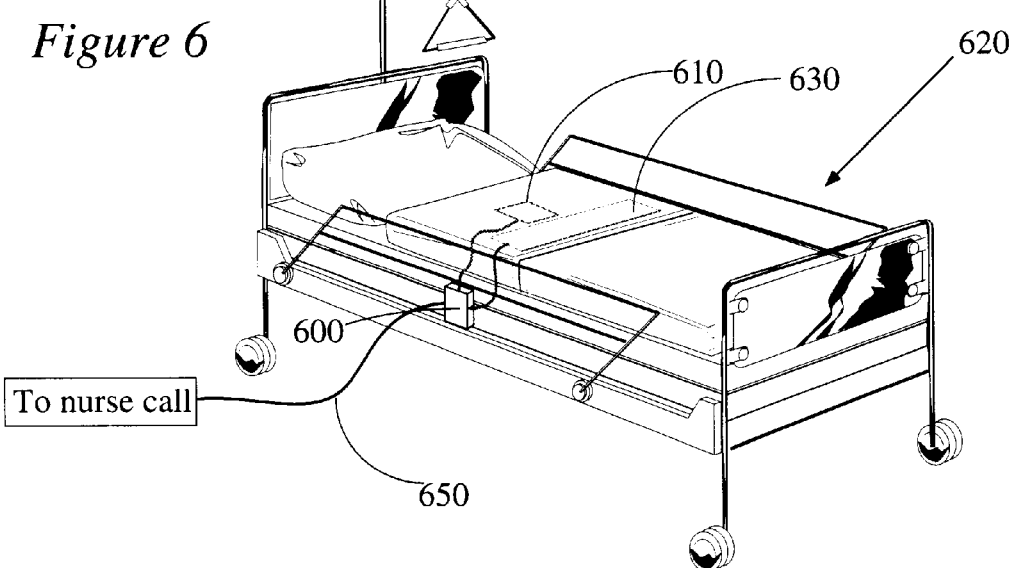
FIG. 6 illustrates the general environment of the instant invention.

Turning first to FIG. 6 wherein the general environment of the instant invention is illustrated, in a typical arrangement a wetness monitor 610 is placed on a hospital bed 620 where it will lie beneath the bedding in an area of the bed that would be expected to receive moisture in the event of a discharge of urine or other electrolytic bodily fluids. Although FIG. 6 illustrates the instant invention as it would be used on a hospital bed, its usefulness is not limited to use in that one setting. For example, it could also be used to detect fluid emissions from seated patients (e.g., be installed in the seat of a chair).

Generally speaking, the sensor 610/monitor 600 combination works as follows. When a patient is placed atop the sensor 610, it will initially be in a "dry" condition and an internal electrical circuit will be in an "open" state, where the term "open" is used in its broadest sense to refer to a relatively non-conductive state. If the patient urinates while in the bed, the bedding near the source of the emission will become saturated with urine. The sensor 610 will draw—preferably by capillary action—fluids from the bedding into its interior where the electrolyte will function to close the otherwise-open electrical circuit, which closure is sensed by the attached electronic patient monitor 600. The patient monitor then signals the care giver per its pre-programmed instructions (e.g., audible and/or visual alarm, signal to the nurses station, etc.). Note that the instant monitor may host a number of electrical connections including, by way of example only, a nurse call connection 650, a connection to a pressure sensitive bed-monitor 630, a computer interface connection (e.g., a serial port) to allow access to the monitor 600 soft/firmware, and a monitor power cord—and a power line, although the monitor 600 can certainly be configured to be battery operated. Further note that the term "closed" circuit will be used in its broadest sense hereinafter to refer to a state of the switch which is relatively more conductive than the "open" or dry state discussed previously.

Preferred Switch Embodiments

A first preferred embodiment of the instant sensor 610 is illustrated in FIG. 1, which contains a plan view of the device. As is illustrated there, in the preferred embodiment the sensor 610 is configured in a "sandwich" arrangement, with a non-conductive/non-porus upper layer 100 situated above a (preferably) larger sized insulating porus member 110. Not shown in this figure is the lower non-conductive/non-porus lower layer 120, which will discussed in more detail in connection with the embodiment of FIG. 2. Note that the outer surface 107 of upper layer 100 is non-conductive to electricity, thereby shielding the patient from contact with the electrical leads 145.

A primary design consideration of the instant sensor/switch 610 is that the patient should be protected from exposure to electricity when the switch becomes wet. To that end, as a general principle all of the embodiments discussed hereinafter have the general characteristic that their exterior faces are non-conductive, and that the conductive elements of the switch are kept between these non-conductive members, thereby shielding the patient from direct contact with the electrically conductive components.

A two-element electrical conductor 147 is divided into electrically isolated leads 145 for purposes which will be made clear below. Weld points 150 hold the sensor sandwich 610 together and need not actually be formed by welding (or heat), but more generally could be fastened together with adhesives such as epoxies or any other suitable means. It is critical, though, that the center of the insulating member 110 be in fluid communication with the exterior of the sensor. Otherwise, liquids could not be drawn into the switch where they close the sensing circuit as described below.

Turning now to FIG. 2, this diagram illustrates the various components of the embodiment of FIG. 1 in greater detail. In the present embodiment, the inner surface 105 of upper member 100 has been treated to make it completely conductive, although those of ordinary skill in the art will recognize that the inner surface 105 could as easily have been made completely non-conductive and the device would work similarly. (See the discussion of FIG. 4 hereinafter). In the preferred embodiment conductive surface 105 will have been treated with aluminum via the process of vacuum deposition. As described previously, except for this aluminized surface deposit the member 100 remains non-conductive to electricity. Insulating center member 110 is oversized to continuously cover and separate the inner surfaces (105 and 135) two outer members (100 and 120, respectively) when they are placed face-to-face as in FIG. 1. Note that the material chosen for this member 110 must be both non-conductive and porus, as the instant invention relies on capillary force to draw the electrolytic fluid into the heart of the switch 610. Note also that in the preferred embodiment, the central porus member 110 is sized to be larger than the non-porous upper 110 and lower members 130, thereby increasing the contact area between the instant device 100 and the patient. Clearly, though, this is not a requirement and the central member 110 could be sized to be the same size or smaller than one, the other, or both of the upper 110 and lower 130 members.

The heart of the instant embodiment is the arrangement of two separated conductive regions 130 and 140. Except for these two regions, the remainder of the inner face 135 of lower member 120 is non-conductive. Although this sort of conductive pattern might be formed in many ways, a preferred way of doing so is to treat the entire surface 135 of lower member 120 and then remove (by, for example, abrasion or electro-chemical action) portions of the conductive matter deposited on the surface, thereby uncovering the non-conductive member 120 lying underneath it. Alternatively, the conductive areas might be created by conventional screening processes using conductive (e.g., carbon based) inks. However the conductive areas are created and for purposes of the instant invention, there must be at least two such isolated conductive regions on one inner face 135 or 105, or at least one isolated conductive region on each.

Note that each electrical lead 145 is placed into electrical communication with a different isolated conductive region. This particular arrangement of conductive regions has the following consequences for wetness sensing: the sensor 610 will not activate until capillary force draws sufficient liquid into the switch to bridge the electrical gap between conductive region 130 and inner surface 105 and between conductive region 140 and inner surface 105. At that time, an attached monitor 600 will sense the closed circuit and sound an alarm per its pre-programmed instructions.

The importance of this arrangement is as follows. By requiring the insulating member 110 to effectively be bridged in two locations, there is a greater degree of confidence that an event is a true "wetness" condition, as opposed to a "dampness" condition which might be caused by, for example, perspiration. This observation is key to the invention disclosed herein: by varying the geometry of the conductive regions in relation to each other it is possible to adjust the sensitivity of the switch, thereby creating a minimal threshold wetness level below which the alarm will not sound.

Figure 3A:
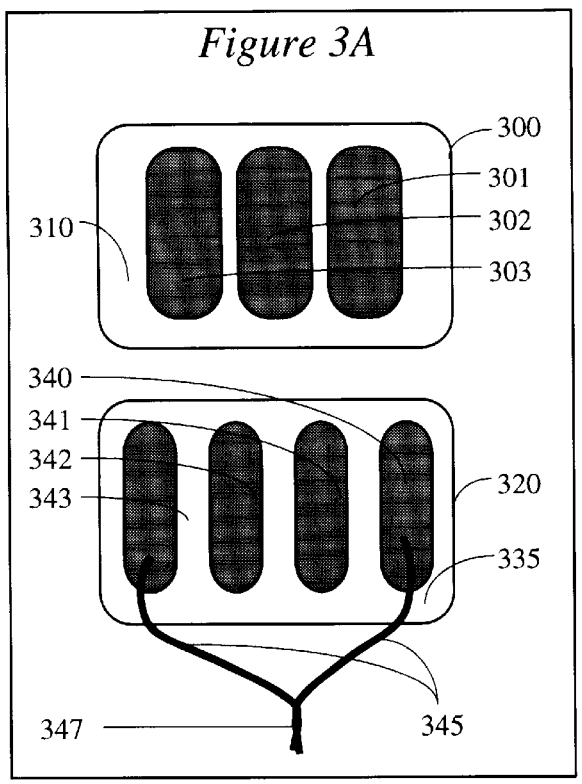
FIG. 3 illustrates another preferred arrangement of conducting and non-conducting regions within the wetness monitor.
Figure 3B:
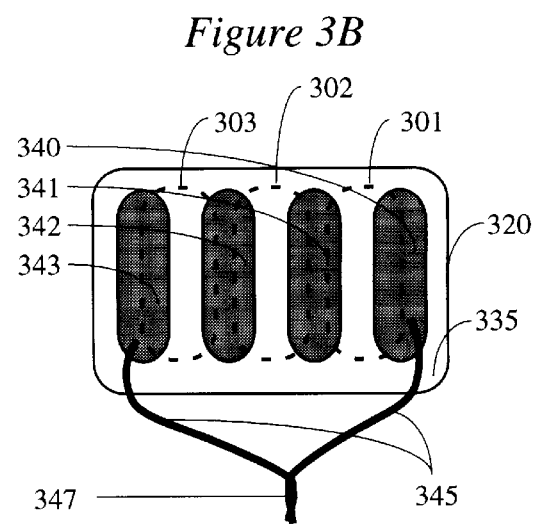

In keeping with this observation, consider the embodiment disclosed in FIGS. 3A and 3B. In this case, the inner face 335 of lower member 320 contains four conductive regions, whereas the inner face 310 of upper member 300 contains three regions. When the switch is assembled as is illustrated in FIG. 3B (the central insulating layer has been omitted for purposes of clarity), note that the three regions on the upper surface (301, 302, and 303) span the interstices between lower member 320 conductive regions 340, 341, 342, and 343. Further note that the conductive leads 345 are in electrical communication with conducting regions positioned at opposite ends of the switch. In order for this switch to signal the presence of moisture, there would need to be enough liquid to bridge the 340–301 gap, the 301–341 gap, the 341–302 gap, the 341–303 gap, and the 303–343 gap. In short, the switch would not signal the presence of moisture until it was almost completely soaked throughout. This, of course, would eliminate many false alarms, but possibly at the expense of missing some legitimate wetness conditions. However, this sort of flexibility in design has not heretofore been available.

Figure 4B:
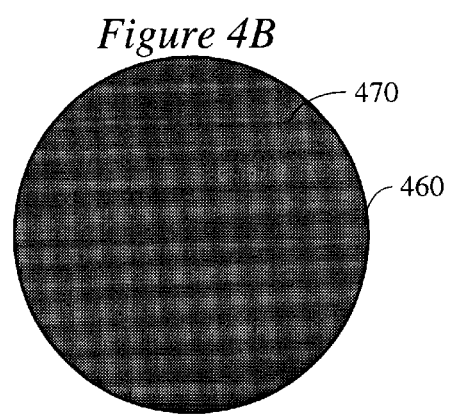
FIG. 4 illustrates still another preferred arrangement of conducting and non-conducting regions within the wetness monitor.
Figure 4A:
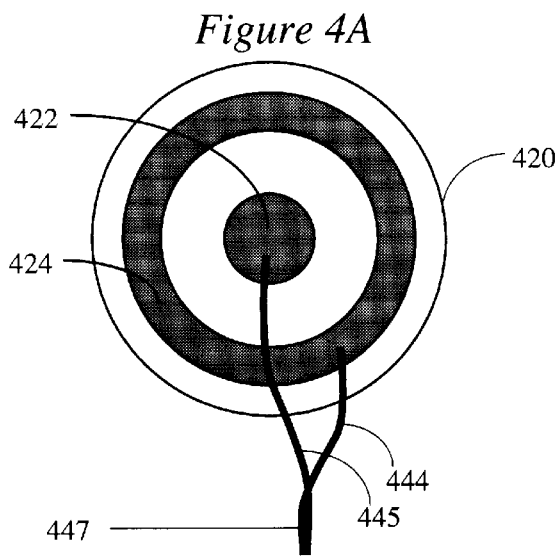
Figure 4C:
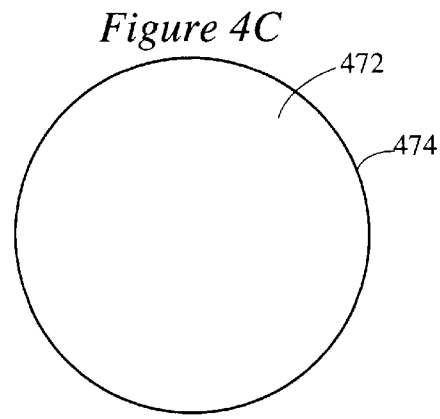

Turning now to another preferred embodiment and is as illustrated in FIG. 4, there is provided an embodiment wherein liquid is drawn from the exterior of the device toward the outer perimeter of inner conductive region 422. In another variation and as is illustrated in FIG. 4C, the inner face 472 of the upper member 474 is completely non-conductive. In this case, the only conductive pathway for electricity moving between electrical leads 444 and 445 is provided by the liquid soaked insulating member (not shown) when fluid bridges the gap between the inner 422 and outer 424 conductive regions. Note that neither of these embodiments is sensitive to the direction from which the liquid is drawn: its response to liquid invasion is symmetric about its center point.

Figure 5:
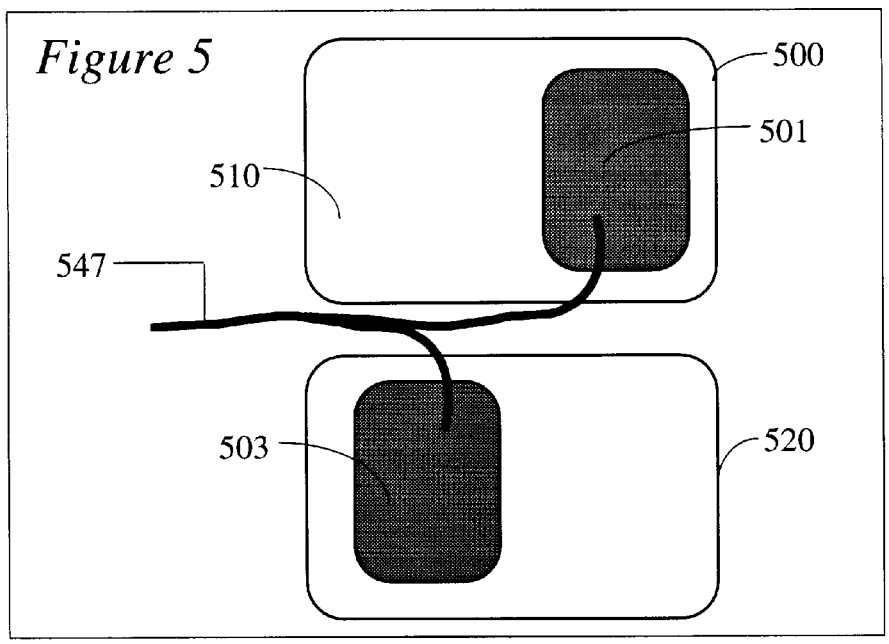
FIG. 5 illustrates still a further preferred arrangement of conducting and non-conducting regions within the wetness monitor.

FIG. 5 contains a final example of still another configuration that would be suitable for use with the instant invention. In this figure, the inner face 510 of upper member 500 contains a single conductive region 501 placed thereon. There is a similar conductive region 503 on the inner face of lower member 520 which is offset from conductive region 501 by some predetermined amount which can be related to the ultimate sensitivity of the switch. (Note that, as before, for purposes of convenience the central insulating member has not been shown.) This switch will not "close" until electrolytic fluid within the central insulating member bridges the nonconductive gap between conductive regions 501 and 503 in at least one place. By varying the distance between the conductive the switch designer can raise the minimum wetness threshold at which the switch will respond. In the most extreme case, the conducting regions could be small "dots" placed at opposite ends of the members 500 and 520. This switch would only close when the insulating central member was completely wet and provided a conductive path from one end of the switch to the other. On the other hand, if the upper and lower conductive members completely covered their respective inner faces, the switch to respond to moisture at any point in the switch. Many false alarms could result in this case. However, the designer might choose this model depending on the needs of the particular application.

Clearly, many variations of this and the previous arrangements are possible and have been specifically contemplated by the instant inventor.

Further Switch Embodiments

Finally, it should be noted that a key feature of the instant invention is that patient must be protected from exposure to electrical current when urine is present. To that end, those skilled in the art will recognize that it is possible that the non-conductive upper half of the embodiments pictured in FIGS. 2, 3, and 4 could be eliminated completely, in which case the switch would consist of a lower member and a porus non-conducting member that covers the electrical elements. The embodiment of FIGS. 4A/4C makes it clear that, in certain configurations, the upper non-conductive layer serves no function except to shield the patient against electrical exposure. If the device were turned so that the electrical element faced away from the patient (e.g., it was placed face down in FIG. 6) the electrically conductive portion of the would not be a risk to the patient, but the various switch patterns would work as described previously where the facing member was completely non-conductive (e.g., FIG. 4C).

Preferred Patient Monitor Embodiments

Turning now to a preferred embodiment of a monitor 600 for use with the instant wetness sensing switch, a primary concern is protection of the patient from exposure to dangerous levels of electrical current when the switch becomes wet. It is commonplace for electronic monitors of this general sort to test the electrical leads by placing a constant DC electrical load thereon. By measuring the resistance across the leads, it is then possible to determine when fluids are present: the measured resistance will decrease markedly. However, this approach exposes the patient to a risk of galvanic burn from the DC current, and this is especially true if the detector switch has electrical elements that can come into contact with the patient's skin.

Figure 7:
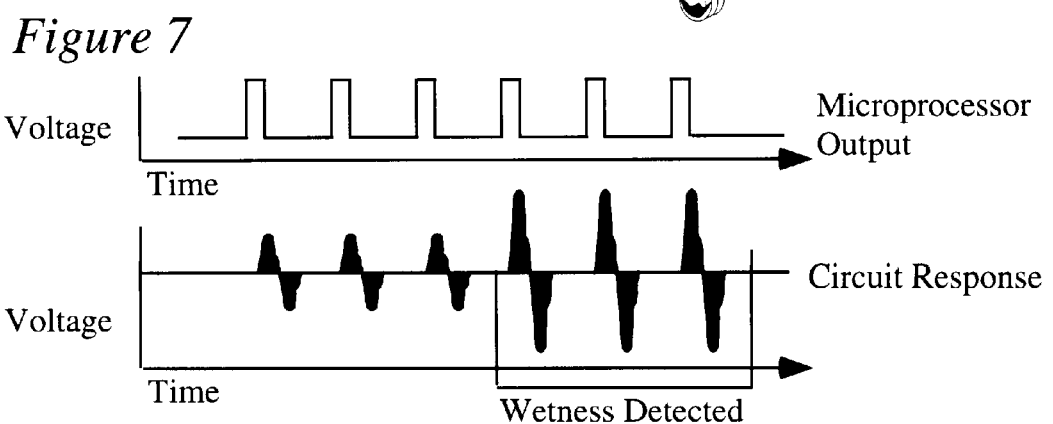
FIG. 7 contains a typical source pulse and circuit response for dry and wet conditions.

The approach taken by the preferred electrical monitor 600 is graphically illustrated in FIG. 7. Rather than place a constant load across the isolated electrical leads, the preferred embodiment "pulses" the leads with a series of voltage spikes (the "microprocessor output" curve in FIG. 7). The response of the sensor circuit will, of course, not be a spike but will instead be some other function of voltage (e.g., the "circuit response" curve of FIG. 7). However, when the attached switch becomes wet the overall magnitude of the response will change, thereby making it possible to detect when the sensor circuit is closed.

Figure 8:
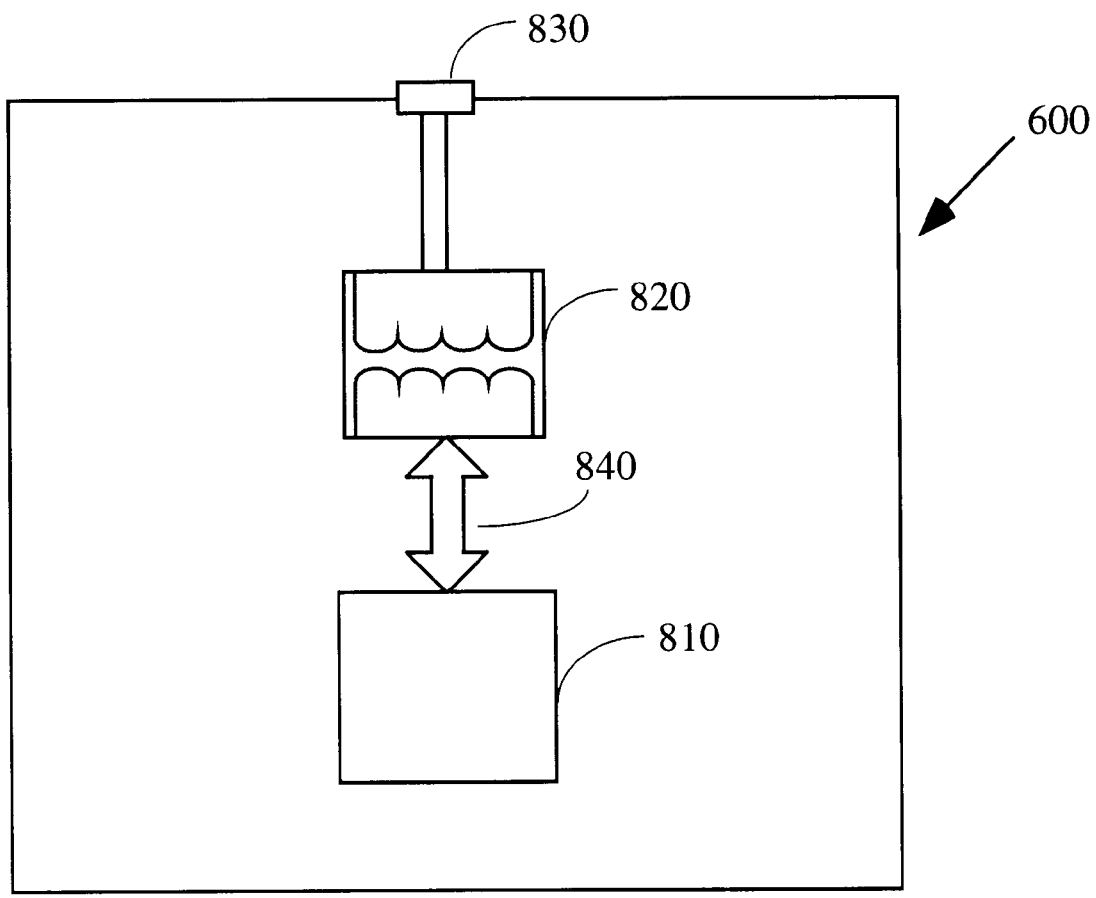
FIG. 8 contains a schematic illustration of a preferred electronic monitor for use with the instant invention.

Turning now to FIG. 8 wherein the components of a preferred monitor 600 arrangement are illustrated, the monitor 600 is equipped with a microprocessor 810 that is in electrical communication with a transformer 820. The CPU 810 generates the pulses that the pass through transformer 820 before being sent to connector 830 and then on to electrical conductor 147, 347, or 447, etc. This step eliminates the "dc" component of the pulse before it is sent to the instant wetness monitor, thereby further protecting the patient against the galvanic risk.

As further protection for the patient, the pulsed sensing voltage of the monitor may be completely stopped if a wetness condition is detected. Of course, it is preferable that the monitor continue to sound the alarm in that case. If this done, the risk of exposing the wet patient to electrical current will then be virtually nonexistent.

Conclusions

Although the preceding text has occasionally referred to the electronic monitor of the instant invention as a "bed"

monitor that was for purposes of specificity only and not out of any intention to limit the instant invention to that one application. In fact, the potential range of uses of this invention is much broader than bed-monitoring alone and might include, for example, use with a chair monitor, or other patient monitor applications, each of which is configurable as a binary switch, a binary switch being one that is capable of sensing at least two conditions and responding to same via distinct electronic signals. In the preferred embodiment, those two conditions would be the presence of wetness and the absence of a wetness from a monitored area. Additionally, it should be noted that the use of the term "binary" is not intended to limit the instant invention to use only with sensors that can send only two signal types. Instead, binary switch will be used herein in its broadest sense to refer to any sort sensor that can be utilized to sense the condition or location of a patient, even if that sensor can generate a multitude of different signals.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A device for detecting a presence of an electrically conductive fluid, comprising:
   (a) a laminar non-conductive impermeable upper member having an inner face, said upper member having at least one upper member edge;
   (b) a laminar non-conductive impermeable lower member having an inner face, said lower member having at least one lower member edge;
   (c) a first conducting region on said lower member inner face;
   (d) a second conducting region on said lower member inner face, said second conducting region being electrically isolated from said first conducting region and separated therefrom by a predetermined distance;
   (e) a porus central insulating member positioned between said inner face of said upper member and said inner face of said lower member,
       said central insulating member at least spanning said predetermined distance between said first and said second conducting regions;
   (f) a first electrical lead in electrical communication with said first conducting region; and,
   (g) a second electrical lead in electrical communication with said second conducting region,
       wherein said first and said second electrical leads are electrically isolated from each other, and,
       wherein said first and said second electrical lead, said first and said second conducting member, and said central insulating member together form an electrical circuit,
       said electrical circuit being an open circuit when the electrically conductive fluid is not present, and,
       said electrical circuit being a closed circuit when the electrically conductive fluid is present.

2. A device for detecting a presence of an electrically conductive fluid according to claim 1, further comprising:
   (h) a third conducting region on said inner face of said upper member,
       said third conducting region spanning at least a portion of said predetermined distance between said first and said second conducting regions.

3. A device for detecting a presence of an electrically conductive fluid according to claim 1, further comprising:
   (i) an electronic patient monitor in electrical communication with at least said first and said second electrical leads,
       said electronic patient monitor being for at least the determination of whether an electrically conductive fluid is present within said central insulating member.

4. A device for detecting a presence of an electrically conductive fluid according to claim 2,
   wherein said third conducting region contains at least two separate electrically isolated upper conducting regions, and
   wherein at least one of said upper conducting regions spans at least as portion of said predetermined distance between said first and said second conductive regions.

5. A device for detecting a presence of an electrically conductive fluid according to claim 1,
   wherein said first conductive region contains a plurality of separate electrically isolated lower conducting regions, and,
   wherein said first electrical lead is in electrical communication with at least one of said plurality of lower conducting regions.

6. A method of detecting a presence of an electrically conductive fluid, wherein is provided the device of claim 1, comprising the steps of:
   (a) sensing a signal representative of a state of said electrical circuit;
   (b) determining from said sensed signal whether said electrical circuit is in a closed state or in an open state;
   (c) determining that the electrically conductive fluid is present if said electrical circuit is in a closed state;
   (d) activating an alarm if the electrically conductive fluid is present; and,
   (e) performing steps (a) to (d) as necessary to monitor for a presence of the electrically conductive fluid.

7. A method according to claim 6, wherein step (a) includes the steps of:
   (a1) applying a pulsed voltage to said first and said second electric leads, and,
   (a2) monitoring a response to said pulsed voltage, thereby sensing a signal representative of a state of said electrical circuit.

8. A device for detecting a presence of an electrically conductive fluid according to claim 1,
   wherein said upper member and said lower member are substantially circular in shape.

9. A device for detecting a presence of an electrically conductive fluid according to claim 1,
   wherein said at least a portion of said central insulating member extends beyond at least one of said upper member edges, or
   wherein at least a portion of said central insulating member extending beyond at least one of said lower member edges.

10. A sensing device for detecting a presence of an electrically conductive fluid such as urine,
    said sensing device having an interior and an exterior, comprising:

(a) a laminar non-conductive impermeable upper member having an inner face, said upper member inner face defining at least a portion of said interior of said sensing device;
(b) a laminar non-conductive impermeable lower member having an inner face, said lower member inner face defining at least a portion of said interior of said sensing device;
(c) a first conducting region on said lower member inner face;
(d) a second conducting region on said inner face of said upper member;
(e) a porus central insulating member positioned between said inner face of said upper member and said inner face of said lower member,
    said central insulating member separating at least said first conducting region and said second conducting region, and,
    wherein said central insulating member is in fluid communication with said exterior of said sensing device;
(f) a first electrical lead in electrical communication with said first conducting region; and,
(g) a second electrical lead in electrical communication with said second conducting region,
    wherein said first and second electrical leads are electrically isolated from each other.

11. A sensing device according to claim 10,
wherein said first conductive region is composed of at least two separate electrically isolated lower conducting regions, and
wherein said first electrical lead is in electrical communication with at least one of said isolated lower conducting regions.

12. A sensing device according to claim 11,
wherein said second conductive region is composed of at least two separate electrically isolated upper conducting regions, and
wherein said second electrical lead is in electrical communication with at least one of said isolated upper conducting regions.

13. A device for detecting a presence of an electrically conductive fluid according to claim 10, further comprising:
(h) an electronic patient monitor in electrical communication with at least said first and second electrical leads, said electronic patient monitor being for at least the determination of whether an electrically conductive fluid is present within said central insulating member.

14. A device for detecting a presence of an electrically conductive fluid according to claim 10,
wherein said first and said second electrical leads, said first and second conductive regions, and said porus central insulating members together form an electrical circuit.

15. A method of detecting a presence of an electrically conductive fluid, wherein is provided the device of claim 14, comprising the steps of:
(a) sensing a signal representative of a state of said electrical circuit;
(b) determining from said sensed signal whether said electrical circuit is in a closed state or in an open state;
(c) determining that the electrically conductive fluid is present if said electrical circuit is in a closed state;
(d) activating an alarm if the electrically conductive fluid is present; and,
(e) performing steps (a) to (d) as necessary to monitor for a presence of the electrically conductive fluid.

16. A method according to claim 15, wherein the step (a) includes the steps of:
(a1) applying a pulsed voltage to said first and said second electric leads, and,
(a2) monitoring a response to said pulsed voltage, thereby sensing a signal representative of a state of said electrical circuit.

* * * * *